United States Patent
Liu

(10) Patent No.: US 10,883,956 B2
(45) Date of Patent: Jan. 5, 2021

(54) ELECTROCHEMICAL SENSOR FOR ANALYTE DETECTION

(71) Applicant: CASE WESTERN RESERVE UNIVERSITY, Cleveland, OH (US)

(72) Inventor: Chung-Chiun Liu, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 15/314,380

(22) PCT Filed: May 26, 2015

(86) PCT No.: PCT/US2015/032399
§ 371 (c)(1),
(2) Date: Nov. 28, 2016

(87) PCT Pub. No.: WO2015/183792
PCT Pub. Date: Dec. 3, 2015

(65) Prior Publication Data
US 2017/0102350 A1    Apr. 13, 2017

Related U.S. Application Data

(60) Provisional application No. 62/003,205, filed on May 27, 2014, provisional application No. 62/084,188, filed on Nov. 25, 2014.

(51) Int. Cl.
*G01N 27/327* (2006.01)
*G01N 33/543* (2006.01)
*G01N 33/573* (2006.01)

(52) U.S. Cl.
CPC ..... *G01N 27/3276* (2013.01); *G01N 33/5438* (2013.01); *G01N 33/573* (2013.01); *G01N 2333/99* (2013.01)

(58) Field of Classification Search
CPC ........... G01N 27/3276; G01N 33/5438; G01N 33/573; G01N 2333/99; G01N 33/574; G01N 33/57407; G01N 33/57434
See application file for complete search history.

(56) References Cited

U.S. PATENT DOCUMENTS

2003/0155241 A1* 8/2003 Lai ..................... G01N 27/4045
204/461
2004/0106190 A1    6/2004 Yang et al.
(Continued)

FOREIGN PATENT DOCUMENTS

EP    2492351 A2    8/2012
WO    2003/040694 A2    5/2003
(Continued)

OTHER PUBLICATIONS

Katz et al. "Biomolecule-functionalized carbon nanotubes: applications in nanobioelectronics". ChemPhysChem, 5(8):p. 1084-1104, (Year: Aug. 20, 2004).*
(Continued)

*Primary Examiner* — J. Christopher Ball
(74) *Attorney, Agent, or Firm* — Tarolli, Sundheim, Covell & Tummino LLP

(57) ABSTRACT

A sensor for the detection of an analyte in a biological sample includes a substrate, a working electrode and counter electrode formed on a surface of the substrate, and a receptor functionalized or chemically functionalized to a surface of an exposed portion of the working electrode. The receptor can selectively bind to the analyte of interest and the analyte once bound is detectable by measuring the current flow between the working electrode and counter electrode.

7 Claims, 2 Drawing Sheets

(56) References Cited

U.S. PATENT DOCUMENTS

| | | | |
|---|---|---|---|
| 2004/0194302 A1* | 10/2004 | Bhullar | C12Q 1/001 29/847 |
| 2006/0272957 A1 | 12/2006 | Lee et al. | |
| 2008/0026394 A1* | 1/2008 | Labgold | C12Q 1/6886 435/6.14 |
| 2008/0035180 A1 | 2/2008 | Mutharasan et al. | |
| 2011/0155576 A1 | 6/2011 | Hwang et al. | |
| 2011/0210017 A1 | 9/2011 | Lai et al. | |
| 2012/0061259 A1 | 3/2012 | Lin et al. | |
| 2013/0065257 A1 | 3/2013 | Wang et al. | |
| 2014/0011691 A1 | 1/2014 | Sierks et al. | |
| 2016/0022185 A1* | 1/2016 | Agarwal | G01N 33/5438 600/345 |

FOREIGN PATENT DOCUMENTS

| | | | | |
|---|---|---|---|---|
| WO | 2004/021000 A1 | 3/2004 | | |
| WO | 2004/061418 A2 | 7/2004 | | |
| WO | WO-2013136115 A1 * | 9/2013 | | B01L 3/5027 |
| WO | 2014/032044 A1 | 2/2014 | | |
| WO | 2014032044 A1 | 2/2014 | | |

OTHER PUBLICATIONS

Pingarron, et al. "Electrochemical immunosensor designs for determination of *Staphylococcus aureus* using 3,3-dithiodipropionic acid di(N-succinimidyl ester)-modified gold electrodes," Talanta 77(2): p. 876-881, (Year: Dec. 2008).*

Supplementary European Search Report for Application No. EP 15 79 9021, dated Sep. 14, 2017.

Shen, et al., "An iridium nanoparticles dispersed carbon based thick film electrochemical biosensor and its application for a single use, disposable glucose biosensor", Sensors and Actuators B, vol. 125 (2007) pp. 106-113.

European Office action for Patent Application No. 15799206.6-1118, dated May 8, 2018.

Chinese Office action for Patent Application No. 201580028310.7, dated Jun. 28, 2018.

Pushpa et al., "Role of pyruvate dehydrogenase complex in traumatic brain injury and Measurement of pyruvate dehydrogenase enzyme by dipstick test", Journal of Emergencies, Trauma, and Shock May 2009, vol. 2, No. 2, May 2009 (May 2009), pp. 67-72.

Warriner et al., "A lactate dehydrogenase amperometric pyruvate electrode exploiting direct detection of NAD+ at a poly(3-methylthiopene):poly(phenol red) modified platinum surface", Jan. 1, 1997 (Jan. 1, 1997), pp. 91-99.

Yahui et al., "A New Optimized Spectrophotometric Assay for the Measurement of Pyruvate Dehydrogenase's Activity", Laboratory of Environmental Science, Jul. 6, 2007 (Jul. 6, 2007), pp. 418-421.

Chinese Office action for Patent Application No. 201580038033.8, dated Mar. 19, 2019.

* cited by examiner

ELECTROCHEMICAL SENSOR FOR ANALYTE DETECTION

RELATED APPLICATION

This application claims priority from U.S. Provisional Application Nos. 62/003,205, filed May 27, 2014 and 62/084,188 filed Nov. 25, 2014, the subject matter of which are incorporated herein by reference in their entirety.

BACKGROUND

A typical disposable electrochemical sensor includes a substrate film upon which a layer of conductive material is deposited and patterned to form electrodes. Traditionally electrochemical cells, or biosensors, are comprised of three electrodes, a working electrode or sensing electrode, a reference electrode, and a counter electrode or auxiliary electrode. The working electrode is where the reaction of interest occurs at a fixed applied potential versus the reference electrode. The reference electrode functions to maintain a stable electrical potential on the working electrode. The counter electrode allows current to flow between the working electrode and the counter electrode so as not to disturb the reference electrode function. In cases when the system potential is inherently stable or small fluctuations in potential are not a concern, the reference and counter electrodes can be combined into a single reference/counter electrode paired with a working electrode. In some instances, electrochemical biosensors use amperometry to quantify specific analyte concentration(s). The working electrode provides a response proportional to its exposed surface area. During fabrication, the manufacture closely controls the process variation associated with the working electrode area.

Normally the working electrode is formed from two or more elements. One element is a conductive layer that forms the active element facilitating electron transfer to or from an electro-active species which are generated when the sample is applied to the sensor. A second element is a dielectric layer that defines, along with the first element, the actual dimensions of the working electrode that is in contact with the sample fluid. The second element forms a window over a portion of the conductive layer. Variation in either element may result in a variation in the sensor response. The second element or dielectric layer may therefore directly influence the accuracy of the reading.

In prior art electrodes, the surface areas may be defined by either conductive layer patterning or dielectric layer patterning and registration. There is a need for a means of more accurately defining the sensor's working electrode to simplify the process of forming an accurate biosensor.

SUMMARY

Embodiments described herein relate to electrochemical biosensors that are capable of providing analysis of various analytes or biomolecules using biological recognition elements. The biosensor can produce a signal that is related to the presence or quantity of the analytes being detected in a sample, such as a biological sample. In some embodiments, the biosensor can be used to detect proteins, polypeptides, cytokines, microorganisms, polynucleotides (mRNA, DNA, cDNA, mRNA, etc.) that are present in a biological sample, such as a bodily fluid (e.g., serum, blood, plasma, saliva, urine, mucous, breath, etc.).

In some embodiments, the biosensor includes a substrate, a working electrode formed on a surface of the substrate, a counter electrode formed on the surface of the substrate, and a dielectric layer covering a portion of the working electrode and counter electrode and defining an aperture exposing other portions of the working electrode and counter electrode. The working electrode is functionalized or chemically functionalized to include a receptor(s) for at least one of the analytes of interest. The receptor can bind selectively to one or more of the analytes of interest in the bodily sample.

The detection system can also include a measuring device for applying a voltage potential to the working electrode, counter electrode, and/or reference electrode and measuring the current flow between the working electrode and counter electrode. The interaction of the analyte and the receptor, e.g., the bound analyte, can be detected using electrochemical analytical techniques, such as cyclic voltammetry (CV), differential pulse voltammetry (DPV), to determine the presence of the analyte in the biological sample.

DETAILED DESCRIPTION

Figure 1:
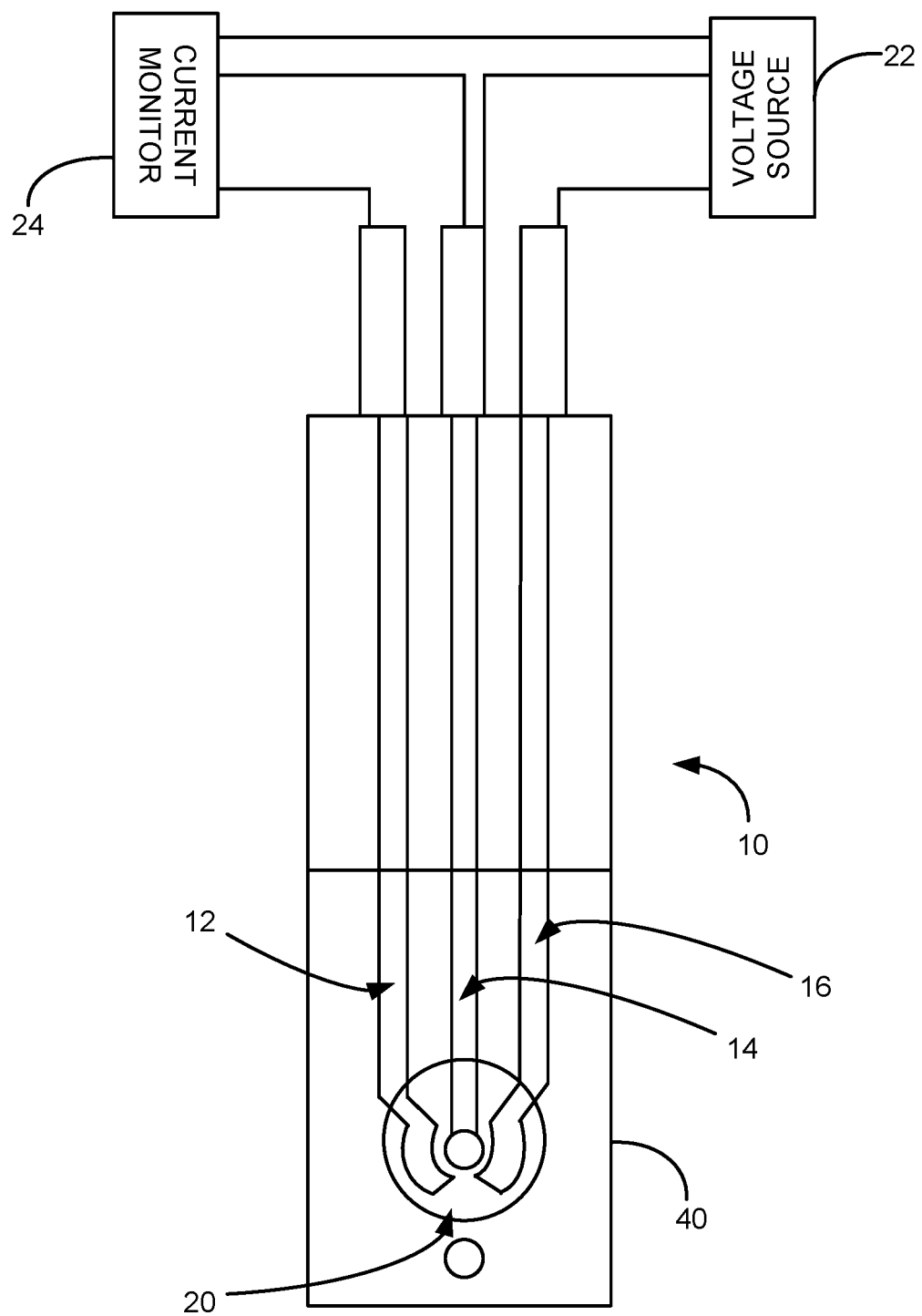
FIG. 1 is a schematic illustration of a biosensor in accordance with an aspect of the application.

Unless specifically addressed herein, all terms used have the same meaning as would be understood by those of skilled in the art of the subject matter of the application. The following definitions will provide clarity with respect to the terms used in the specification and claims.

As used herein, the term "monitoring" refers to the use of results generated from datasets to provide useful information about an individual or an individual's health or disease status. "Monitoring" can include, for example, determination of prognosis, risk-stratification, selection of drug therapy, assessment of ongoing drug therapy, determination of effectiveness of treatment, prediction of outcomes, determination of response to therapy, diagnosis of a disease or disease complication, following of progression of a disease or providing any information relating to a patient's health status over time, selecting patients most likely to benefit from experimental therapies with known molecular mechanisms of action, selecting patients most likely to benefit from approved drugs with known molecular mechanisms where that mechanism may be important in a small subset of a disease for which the medication may not have a label, screening a patient population to help decide on a more invasive/expensive test, for example, a cascade of tests from a non-invasive blood test to a more invasive option such as biopsy, or testing to assess side effects of drugs used to treat another indication.

As used herein, the term "quantitative data" or "quantitative level" or "quantitative amount" refers to data, levels, or amounts associated with any dataset components (e.g., markers, clinical indicia,) that can be assigned a numerical value.

As used herein, the term "subject" refers to a human or another mammal. Typically, the terms "subject" and "patient" are used herein interchangeably in reference to a human individual.

As used herein, the term "bodily sample" refers to a sample that may be obtained from a subject (e.g., a human) or from components (e.g., tissues) of a subject. The sample may be of any biological tissue or fluid with, which analytes described herein may be assayed. Frequently, the sample will be a "clinical sample", i.e., a sample derived from a patient. Such samples include, but are not limited to, bodily fluids, e.g., saliva, breath, urine, blood, plasma, or sera; and archival samples with known diagnosis, treatment and/or outcome history. The term biological sample also encompasses any material derived by processing the bodily sample. Processing of the bodily sample may involve one or more of, filtration, distillation, extraction, concentration, inactivation of interfering components, addition of reagents, and the like.

As used herein, the terms "normal" and "healthy" are used interchangeably. They refer to an individual or group of individuals who have not shown any symptoms of a disease, condition, or pathology to be detected, and have not been diagnosed with the disease, condition, or pathology. Preferably, the normal individual (or group of individuals) is not on medication. In certain embodiments, normal individuals have similar sex, age, body mass index as compared with the individual from, which the sample to be tested was obtained. The term "normal" is also used herein to qualify a sample isolated from a healthy individual.

As used herein, the terms "control" or "control sample" refer to one or more biological samples isolated from an individual or group of individuals that are normal (i.e., healthy). The term "control", "control value" or "control sample" can also refer to the compilation of data derived from samples of one or more individuals classified as normal.

Embodiments described herein relate to electrochemical biosensors that are capable of providing analysis of various analytes or biomolecules using biological recognition elements. The biosensor can produce a signal that is related to the presence or quantity of the analytes being detected in a sample, such as a biological sample. In some embodiments, the biosensor can be used to detect proteins, polypeptides, cytokines, microrganisms, polynucleotides (mRNA, DNA, cDNA, mRNA, etc.) that are present in a biological sample, such as a bodily fluid (e.g., serum, blood, plasma, saliva, urine, mucous, breath, etc.). The biosensors described herein can provide a single use, disposable, and cost-effective means for simple point-of-care, real time assessment of analytes in biological samples, such as bodily fluids obtained by non-invasive or minimally invasive means.

FIG. 1 illustrates a biosensor 10 in accordance with an embodiment of the application. The sensor 10 is a three-electrode sensor including a counter electrode 12, a working electrode 14, and a reference electrode 16 that are formed on a surface of a substrate. A dielectric layer 40 covers a portion of the working electrode 12, counter electrode 14 and reference electrode 16. The dielectric layer 40 includes an aperture 20 that defines a detection region of the working electrode 12, counter electrode 14, and reference electrode 16, which is exposed to samples containing one or more analytes of interest to be detected. A receptor(s) for at least one analyte of interest can be functionalized or chemically functionalized to the working electrode. The receptor can bind selectively to one or more of the analytes of interest in the biological sample.

The biosensor can also include a voltage source 22 for applying a voltage potential to the working electrode, counter electrode, and/or reference electrode and a measuring device or current monitor 24 for measuring the current flow between the working electrode and counter electrode. The interaction of the analyte and the receptor can be detected using electrochemical analytical techniques, such as cyclic voltammetry (CV), differential pulse voltammetry (DPV), to determine the presence of the analyte in the sample.

The working electrode 14 is poised at an appropriate electrochemical potential such that the current that flows through the electrode changes when the receptor binds to an analyte in the sample. The function of the counter electrode 12 is to complete the circuit, allowing charge to flow through the sensor 10. The working electrode 14 and the counter electrode 12 are preferably formed of the same material, although this is not a requirement. Examples of materials that can be used for the working electrode 14 and counter electrode 12 include, but are not limited to, gold, platinum, palladium, silver, carbon, alloys thereof, and composites thereof.

The receptor, which is functionalized or chemically functionalized to the working electrode, is a molecule that binds selectively to an analyte of interest. A molecule that binds selectively to an analyte is a molecule that binds preferentially to that analyte (i.e., its binding affinity for that analyte is greater than its binding affinity for any other analyte). Its binding affinity for the analyte of interest may be 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 100-fold or more than its binding affinity for any other analyte. In addition to its relative binding affinity, the receptor must also have an absolute binding affinity that is sufficiently high to efficiently bind the analyte of interest (i.e., it must have a sufficient sensitivity). Receptors having binding affinities in the picomolar to micromolar range are suitable. Such interaction can be reversible.

The receptor may be of any nature (e.g., chemical, nucleic acid, peptide, lipid, combinations thereof and the like). The analyte too may be of any nature provided there exists a receptor that binds to it selectively and in some instances specifically. In some embodiments, the analyte can be a charged species or molecule.

The term "functionalized" or "chemically functionalized," as used herein, means addition of functional groups onto the surface of a material by chemical reaction(s). As will be readily appreciated by a person skilled in the art, functionalization can be employed for surface modification of materials in order to achieve desired surface properties, such as biocompatibility, wettability, and so on. Similarly, the term "biofunctionalization," "biofunctionalized," or the like, as used herein, means modification of the surface of a material so that it has desired biological function, which will he readily appreciated by a person of skill in the related art, such as bioengineering.

The receptors may be functionalized to the working electrode covalently or non-covalently. Covalent attachment of a receptor to working electrode may be direct or indirect (e.g., through a linker). Receptors may be immobilized on the working electrode using a linker. The linker can be a linker that can be used to link a variety of entities.

In some embodiments, the linker may be a homo-bifunctional linker or a hetero-bifunctional linker, depending upon the nature of the molecules to be conjugated. Homo-bifunctional linkers have two identical reactive groups. Hetero-bifunctional linkers have two different reactive groups. Various types of commercially available linkers are reactive with one or more of the following groups: primary amines, secondary amines, sulphydryls, carboxyls, carbonyls and carbohydrates. Examples of amine-specific linkers are bis (sulfosuccinimidyl) suberate, bis[2-(succinimidooxycarbonyloxy)ethyl]sulfone, disuccinimidyl suberate, disuccinimidyl tartarate, dimethyl adipimate 2HCl, dimethyl pimelimidate 2HCl, dimethyl suberimidate HCl, ethylene glycolbis-[succinimidyl-[succinate]], dithiolbis(succinimidyl propionate), and 3,3'-dithiobis(sulfosuccinimidylpropionate). Linkers reactive with sulfhydryl groups include bismaleimidohexane, 1,4-di-[3'-(2'-pyridyldithio)-propionamido)]butane, 1-[p-azidosalicylamido]-4-[iodoacetamido] butane, and N-[4-(p-azidosalicylamido)butyl]-3'-[2'-pyridyldithio]propionamide. Linkers preferentially reactive with carbohydrates include azidobenzoyl hydrazine. Linkers preferentially reactive with carboxyl groups include 4-[p-azidosalicylamido]butylamine.

Heterobifunctional linkers that react with amines and sulfhydryls include N-succinimidyl-3-[2-pyridyldithio]propionate, succinimidyl[4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional linkers that react with carboxyl and amine groups include 1-ethyl-3-[3-dimethylaminopropyl]-carbodiimide hydrochloride. Heterobifunctional linkers that react with carbohydrates and sulfhydryls include 4-[N-maleimidomethyl]-cyclohexane-1-carboxylhydrazide HCl, 4-(4-N-maleimidophenyl)-butyric acid hydrazide 2HCl, and 3-[2-pyridyldithio]propionyl hydrazide.

Alternatively, receptors may be non-covalently coated onto the working electrode. Non-covalent deposition of the receptor to the working electrode may involve the use of a polymer matrix. The polymer may be naturally occurring or non-naturally occurring and may be of any type including but not limited to nucleic acid (e.g., DNA, RNA, PNA, LNA, and the like, or mimics, derivatives, or combinations thereof), amino acids (e.g., peptides, proteins (native or denatured), and the like, or mimics, derivatives, or combinations thereof, lipids, polysaccharides, and functionalized block copolymers. The receptor may be adsorbed onto and/or entrapped within the polymer matrix.

Alternatively, the receptor may be covalently conjugated or crosslinked to the polymer (e.g., it may be "grafted" onto a functionalized polymer).

An example of a suitable peptide polymer is poly-lysine (e.g., poly-L-lysine). Examples of other polymers include block copolymers that comprise polyethylene glycol (PEG), polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes, alkyl cellulose, hydroxyalkyl celluloses, cellulose ethers, cellulose esters, nitrocelluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, polyvinyl chloride, polystyrene, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate), poly(lactide-glycolide), copolyoxalates, polycaprolactones, polyesteramides, polyorthoesters, polyhydroxybutyric acid, polyanhydrides, poly(styrene-b-isobutylene-b-styrene) (SIBS) block copolymer, ethylene vinyl acetate, poly(meth)acrylic acid, polymers of lactic acid and glycolic acid, polyanhydrides, poly(ortho)esters, polyurethanes, poly(butic acid), poly(valeric acid), and poly (lactide-cocaprolactone), and natural polymers such as alginate and other polysaccharides including dextran and cellulose, collagen, albumin and other hydrophilic proteins, zein and other prolamines and hydrophobic proteins, copolymers and mixtures thereof, and chemical derivatives thereof including substitutions and/or additions of chemical groups, for example, alkyl, alkylene, hydroxylations, oxidations, and other modifications routinely made by those skilled in the art.

In one particular embodiment, the working electrode can comprise a gold working electrode that is crosslinked or biotinylated chemically in order to allow attachment of an antibody or biotin containing molecule. The gold working electrode can be cross-linked, for example, with dithiolbis (succinimidyl propionate) (DSP), which contains an amine reactive N-hydroxysuccinimide (NHS) ester that can react with amine groups of proteins and antibodies. Biotinylation can also be used for the attachment of biotin-containing molecules, including biotin containing aptamers, proteins, nucleic acid, or other molecule.

It will be appreciated, the flexibility of the chemical functionalization makes the biosensor useful for attaching essentially any receptor or ligand having an affinity for analytes. Examples of analytes for which receptors or ligands having affinity therefor that may be attached to the working electrode include, but are not limited to DNA, RNA, oligo-nucleotides, proteins, biotin, and streptavidin. The receptors for these analytes functionalized or chemically functionalized to the working electrode can include ligands, such as antibodies or antigen binding fragments thereof. Antibodies, generally have several primary amines in the side chain of lysine (K) residues that can be available for cross-linking, such as NHS-ester cross-linking.

The chemical functionalization method also enables the bioconjugation of DNA aptamers having an amino group. These aptamers could potentially bind small molecules and proteins. Once bound, the change in the charge on the surface of the working electrode would enable the biosensor to detect the target biomolecule or small molecule.

In some embodiments, the receptor can be an antibody specific for an analyte of interest. Suitable antibodies for use in the biosensor described herein include monoclonal and polyclonal antibodies, immunologically active fragments (e.g., Fab or (Fab)2 fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czemik et al., NeuroNeuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S. Neuberger et al., Nature, 1984, 312: 604-608; S. Takeda et al., Nature, 1985, 314: 452-454). Antibodies to be used in the biosensor can be purified by methods well known in the art (see, for example, S. A. Minden, "Monoclonal Antibody Purification", 1996, IBC Biomedical Library Series: Southbridge, Mass.). For example, antibodies can be affinity purified by passage over a column to which a protein marker or fragment thereof is bound. The bound antibodies can then be eluted from the column using a buffer with a high salt concentration.

Instead of being prepared, antibodies to be used in the methods described herein may be obtained from scientific or commercial sources.

In some embodiments, the receptor can be antibody or antigen binding fragment thereof that specifically binds to a cancer biomarker. Examples of cancer biomarkers include AMACR (prostate cancer), Carbohydrate antigen 125 (CA125) (ovarian cancer), human epididymis protein 4 (HE4) (ovarian cancer), BRAC1/BRAC2 (breast cancer, ovarian cancer), AFP (liver cancer), BCR-ABL (chronic myeloid leukemia), BRAF V600E (melanoma/colorectal cancer), KIT (gastrointestinal stromal tumor), PSA (prostate cancer), S100 (melanoma), KRAS (lung cancer), CIZL (lung cancer), and EGFR (colorectal/lung cancer).

It will be appreciated that the receptors are not limited to antibodies or antigen binding fragments to cancer biomarkers and that antibodies or antigen binding fragments to other biomarkers associated with other diseases, disorders, conditions, or pathologies, which can be detectable in a bodily sample can also be functionalized or chemically functionalized to the working electrode.

In order to minimize any non-specific binding on the working electrode surface and blocking any open surface area of the working electrode at least one blocking agent can be applied to the surface of the working electrode once the receptor has been functionalized or chemically functionalized to the working electrode. The blocking agent can enhance the reproducibility and sensitivity of the biosensor by minimizing non-specific interactions on the working electrode. In some embodiments, the blocking agent can include dithiothreitol or casein. The blocking agent can be applied to the surface of the working at an amount effective to minimize non-specific binding of proteins or other molecules on the surface of the working electrode.

The voltage source 22 can apply a voltage potential to the working electrode 14 and reference and/or counter electrode 16, 12, depending on the design of the sensor 10. The current between the working electrode 14 and counter electrode 16 can be measured with the measuring device or meter 24. Such current is dependent on interaction of analyte with the receptor on the working electrode.

The amount or level of current measured is proportional to the level or amount of analyte in the biological sample. In some embodiments, where the sample is a bodily sample obtained from a subject, once the current level generated by the reaction solution tested with the sensor is determined, the level can be compared to a predetermined value or control value to provide information for diagnosing or monitoring of the condition, pathology, or disorder in a subject that is associated with presence or absence of the analyte.

The current level generated by sample obtained from the subject can be compared to a current level of a sample previously obtained from the subject, such as prior to administration of a therapeutic. Accordingly, the methods described herein can be used to measure the efficacy of a therapeutic regimen for the treatment of a condition, pathology, or disorder associated with the level of the analyte in a subject by comparing the current level obtained before and after a therapeutic regimen. Additionally, the methods described herein can be used to measure the progression of a condition, pathology, or disorder associated with the presence or absence of the analyte of interest in a subject by comparing the current level in a bodily sample obtained over a given time period, such as days, weeks, months, or years.

The current level generated by a sample obtained from a subject may also be compared to a predetermined value or control value to provide information for determining the severity or aggressiveness of a condition, pathology, or disorder associated with analyte levels in the subject. A predetermined value or control value can be based upon the current level in comparable samples obtained from a healthy or normal subject or the general population or from a select population of control subjects.

The predetermined value can take a variety of forms. The predetermined value can be a single cut-off value, such as a median or mean. The predetermined value can be established based upon comparative groups such as where the current level in one defined group is double the current level in another defined group. The predetermined value can be a range, for example, where the general subject population is divided equally (or unequally) into groups, or into quadrants, the lowest quadrant being subjects with the lowest current level, the highest quadrant being individuals with the highest current level. In an exemplary embodiment, two cutoff values are selected to minimize the rate of false positive and negative results.

Figure 2:
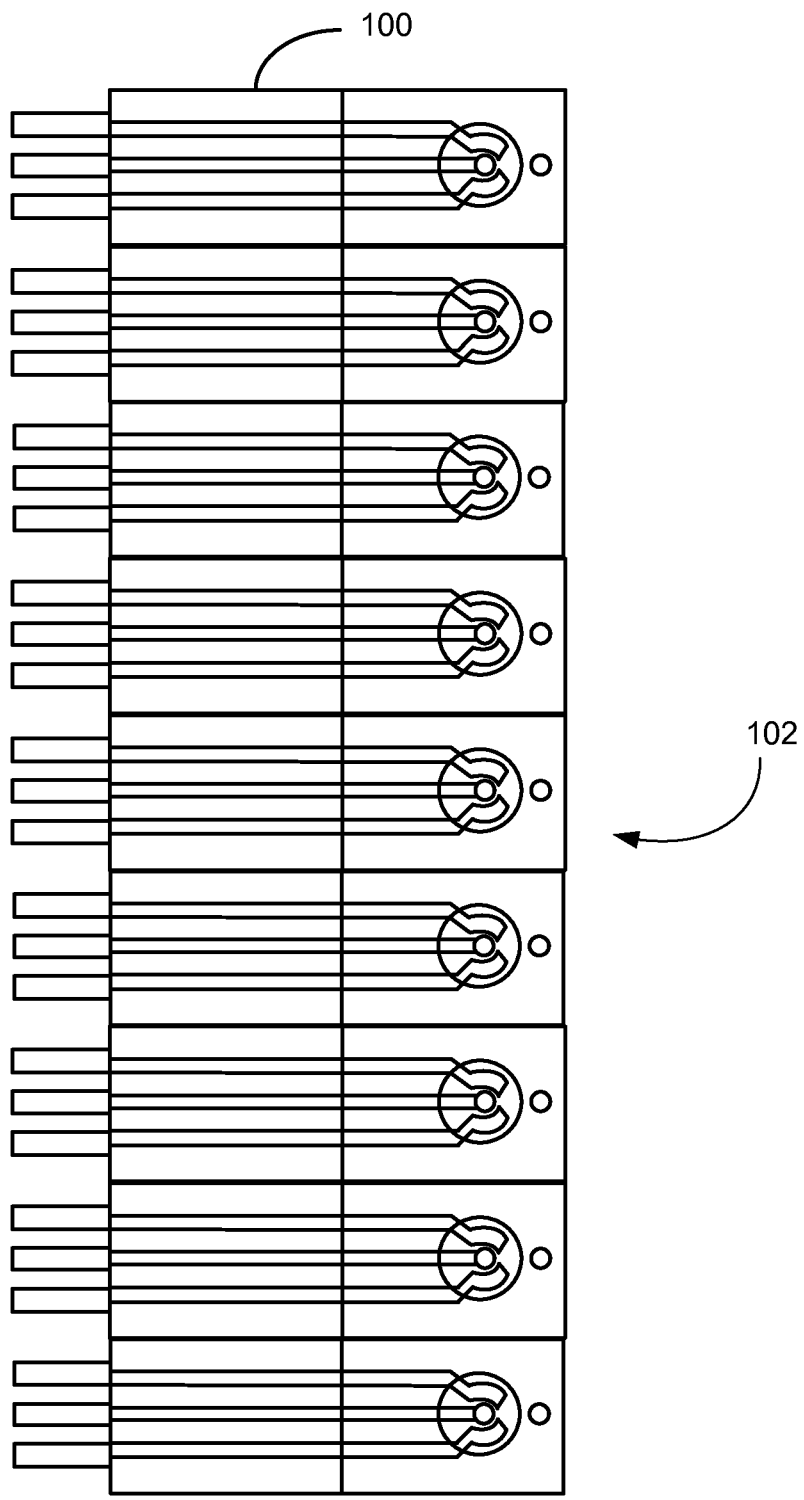
FIG. 2 is a top plan view of an array of biosensors in a row manufactured by a screen-printing process.

The biosensor illustrated in FIGS. 1 and 2 can be fabricated on a substrate 100 formed from polyester or other electrically non-conductive material, such as other polymeric materials, alumina ($Al_2O_3$), ceramic based materials, glass or a semi-conductive substrate, such as silicon, silicon oxide and other covered substrates. Multiple sensor devices 102 can thus be formed on a common substrate 100 (FIG. 2). As will be appreciated, variations in the geometry and size of the electrodes are contemplated.

The biosensor can be made using a thin film, thick film, and/or ink-jet printing technique, especially for the deposition of multiple electrodes on a substrate. The thin film process can include physical or chemical vapor deposition. Electrochemical sensors and thick film techniques for their fabrication are discussed in U.S. Pat. No. 4,571,292 to C. C. Liu et al., U.S. Pat. No. 4,655,880 to C. C. Liu, and application U.S. Ser. No. 09/466,865, which are incorporated by reference in their entirety.

In some embodiments, the working electrode, counter electrode, and reference electrode may be formed using laser ablation, a process which can produce elements with features that are less than one-thousandth of an inch. Laser ablation enables the precise definition of the working electrode, counter electrode, and reference electrode as well as electrical connecting leads and other features, which is required to reduce coefficient of variation and provide accurate measurements. Metalized films, such as Au, Pd, and Pt or any metal having similar electrochemical properties, that can be sputtered or coated on plastic substrates, such as PET or polycarbonate, or other dielectric material, can be irradiated using laser ablation to provide these features.

In one example, a gold film with a thickness of about 300 A to about 2000 A can be deposited by a sputtering technique resulting in very uniform layer that can be laser ablated to form the working and counter electrodes. The counter electrode can use other materials. However, for the simplicity of fabrication, using identical material for both working and counter electrodes will simplify the fabrication process providing the feasibility of producing both electrodes in a single processing step. An Ag/AgCl reference electrode, the insulation layer, and the electrical connecting parts can then be printed using thick-film screen printing techniques.

The working electrode surface can then be cross-linked or biotinylated chemically in order to allow the attachment of an antibody or biotin-contained molecules. The crosslinking step can be accomplished by generating thiol bonds. This can be chemically accomplished using, for example, DSP (Dithiolbis[succinimidyl propionatel]) to produce the thiol bonds. DSP can be dissolved in DMSO, (Dimethyl sulfoxide). DSP contains amine-reactive N-hydroxysuccinimide (NHS) ester at each end of its carbon spacer arm. NHS can react with primary amine (At pH=7-9) forming stable amide bonds. As an example, 1-ethyl-3-(3-dimethylaminopropyl) carbodiimide hydrochloride (EDC) and N-Hydroxysuccinimide (NHS) can be used forming semi-stable amine-reactive ester groups on the DSP modified gold electrode surface. Similar chemical methods can be used to produce semi-stable amine-ester groups to enhance the cross linking between the antibodies and the thiol groups. Other cross-linking agent, such as 3,3'-dithiobis[sulfosuccinimidylpropionate] (DTSSP), can also be used in this process.

Biotinylation is rapid, specific and is normally unperturb to the natural function of the molecule due to the relatively small size of biotin. Streptavidin and similar chemicals such as avidin can be immobilized on the working electrode surface for a biosensor for the detection of an interaction of antibody and antigen.

The working electrode of the biosensor can either be cross-linked or biotinylated with antibody receptor or biotin-contained protein (including antibody) using the immobilization approaches described above.

Following addition of an antibody or protein to the working electrode, the working electrode surface can be blocked using a blocking agent to minimize any non-specific molecule (e.g., protein) bonding on the electrode surface. This step will enhance the reproducibility and sensitivity of the biosensor. In some embodiments, DTT (Dithiothreitol), casein, and/or other blocking agents can be used to cover the open surface area of the working electrode and minimize any non-specific protein coverage.

In other embodiments a plurality of biosensors can be provided on a surface of a substrate to provide a biosensor array. The biosensor array can be configured to detect analyte concentration changes in a host of chemical and/or biological processes (chemical reactions, cell cultures, neural activity, nucleic acid sequencing processes, etc.) occurring in proximity to the array. The biosensor array can include a plurality biosensors arranged in a plurality of rows and a plurality of columns. Each biosensor comprises a working electrode, a counter electrode, and a dielectric layer covering a portion of the working electrode and counter electrode and defining an aperture exposing other portions of the working electrode and counter electrode. A receptor(s) for at least one of the analytes of interest can be functionalized or chemically functionalized to the working electrode. The receptors can be the same or different for each biosensor of the array and can bind selectively to one or more of the analytes of interest. The biosensors of the array can be configured to provide at least one output signal representing the presence and/or concentration of an analyte proximate to a surface of the array. For each column of the plurality of columns or for each row of the plurality of rows, the array further comprises column or row circuitry configured to provide voltage potentials to respective biosensors in the column or row. Each biosensor in the row or column can potentially detect a different analyte and/or biased to detect different analytes.

In one example, the receptor can include an antibody and/or antigen binding fragment thereof that binds to alpha-methylacyl-CoA racemase (AMACR) or a substrate or metabolite of AMACR. AMACR is an enzyme involved in peroxisomal beta-oxidation of dietary branched-chained fatty acids. AMACR has been consistently overexpressed in prostate cancer epithelium, hence it becomes an ideal specific biomarker for cancer cells within the prostate gland. Over-expression of AMACR may increase the risk of prostate cancer, because its expression is increased in premalignant lesions (prostatic intraepithelial neoplasia). Furthermore, epidemiologic, genetic and laboratory studies have pointed to the importance of AMACR in prostate cancer. Genome-wide scans of linkage in hereditary prostate cancer families have demonstrated that the chromosomal region for AMACR (5p 13) is the location of a prostate cancer susceptibility gene and AMACR gene sequence variants (polymorphisms) have been shown to co-segregate with cancer of the prostate in families with hereditary prostate cancer.

In some embodiments, the antibody can be a monoclonal antibody that specifically binds to AMACR. Examples of monoclonal antibodies that bind specifically to AMACR are AMACR Clone 13H4, commercially available from Dako, AMACR antibody, 2A10F3, commercially available from Thermoscientific, and AMACR antibody, 2A10F3, commercially available from Novus.

The antibody or antigen bind fragment thereof that binds to AMACR or a substrate or metabolite of AMACR can be attached to the working electrode covalently or non-covalently by, for example, cross-linking or biotinylation. The interaction of the antibody or antigen binding fragment thereof with AMACR or a substrate or metabolite of AMACR in a biological sample obtained from a subject having or suspected of having prostate cancer will produce a signal which can be detected electrochemically, electrically or optically, and the signal can then be used to quantify AMACR in a biological sample.

The amount or quantity of AMACR in the biological sample obtained from the subject suspected of having or at risk of prostate cancer can be measured using the biosensor to determine the level and quantity of AMACR in the bodily fluid and hence whether the subject has prostate cancer or an increased risk of prostate cancer.

The voltage source can apply a voltage potential to the working electrode and reference and/or counter electrode, depending on the design of the biosensor. The current between the working electrode and counter electrode can be measured with a measuring device or meter.

The amount or level of current measured can be proportional to the amount of AMACR or a substrate or metabolite of AMACR in the biological sample as well as the risk or presence of prostate cancer in the subject. Once the current level generated by the biological sample tested with the biosensor is determined, the level can be compared to a predetermined value or control value to provide information for diagnosing or monitoring of prostate cancer in a subject. For example, the current level can be compared to a predetermined value or control value to determine if a subject is afflicted with or has prostate cancer. An increased current level compared to a predetermined value or control value can be indicative of the subject having prostate cancer;

whereas similar or decreased current level compared to a predetermined value or control value can be indicative of the absence of prostate cancer in the subject The current level generated by the biological sample obtained from the subject can be compared to a current level of a similar biological sample previously obtained from the subject, such as prior to administration of a therapeutic. Accordingly, the methods described herein can be used to measure the efficacy of a therapeutic regimen for the treatment of prostate cancer in a subject by comparing the current level obtained before and after a therapeutic regimen. Additionally, the methods described herein can be used to measure the progression of prostate cancer in a subject by comparing the current level in a biological sample obtained over a given time period, such as days, weeks, months, or years.

The current level generated by a biological sample of the subject may also be compared to a predetermined value or control value to provide information for determining the severity or aggressiveness of the prostate cancer in the subject. Thus, in some aspect, the current level may be compared to control values obtained from subjects with well known clinical categorizations, or stages, of histopathologies related to prostate cancer (e.g., Gleason score of prostate cancer or indolent versus aggressive prostate cancer). In one particular embodiment, the current in a sample can provide information for determining a particular Gleason grade or score of prostate cancer in the subject.

A predetermined value or control value can be based upon the current level in comparable samples obtained from a healthy or normal subject or the general population or from a select population of control subjects. In some aspects, the select population of control subjects can include individuals diagnosed with prostate cancer. For example, a subject having a greater current level compared to a control value may be indicative of the subject having a more advanced stage of a prostate cancer.

The select population of control subjects may also include subjects afflicted with prostate cancer in order to distinguish subjects afflicted with prostate cancer from those with benign prostate disease. In some aspects, the select population of control subjects may include a group of individuals afflicted with prostate cancer.

The predetermined value can take a variety of forms. The predetermined value can be a single cut-off value, such as a median or mean. The predetermined value can be established based upon comparative groups such as where the current level in one defined group is double the current level in another defined group. The predetermined value can be a range, for example, where the general subject population is divided equally (or unequally) into groups, or into quadrants, the lowest quadrant being subjects with the lowest current level, the highest quadrant being individuals with the highest current level. In an exemplary embodiment, two cutoff values are selected to minimize the rate of false positive and negative results.

It will be appreciated that the detection of AMACR can be accomplished using any biological sample or physiological fluid obtained from the subject. Blood samples have been used, and the detection of AMACR can also be achieved using other physiological fluid, such as urine, saliva, and others. Thus, the detection of AMACR as a biomarker of prostate cancer in any type of physiological fluid can be provided by the biosensor described herein.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention the following is claimed:

1. A sensor for the detection of AMACR or an AMACR substrate thereof in a biological sample comprising:
    a substrate;
    a working electrode formed on a surface of the substrate;
    a counter electrode formed on the surface of the substrate;
    a dielectric layer covering a portion of the working electrode and counter electrode and defining an aperture exposing a detection region of the working electrode and counter electrode;
    a measuring device for applying voltage potentials to the working electrode and counter electrode and measuring the current flow between the working electrode and counter electrode; and
    an antibody or antigen binding fragment thereof directly functionalized or chemically functionalized to a surface of the exposed detection region of the working electrode and being configured to selectively bind to AMACR or to the AMACR substrate in the biological sample, and the AMACR or the AMACR substrate once bound being detectable by measuring the current flow between the working electrode and counter electrode, wherein the working electrode and the counter electrode are obtained from sputtering a metalized film on a plastic substrate and irradiating the metalized film using laser ablation to define the dimensions of the working electrode and counter electrode.

2. The sensor of claim 1, wherein the working electrode and counter electrode independently comprise gold, platinum, palladium, silver, carbon, alloys thereof, and composites thereof.

3. The sensor of claim 1, further comprising a reference electrode on the surface of the substrate, the dielectric covering a detection region of the reference electrode.

4. The sensor of claim 1, further comprising a blocking agent that covers open areas of the exposed detection region of the working electrode.

5. The sensor of claim 4, wherein the blocking agent comprises DTT (Dithiothreitol) or casein.

6. The sensor of claim 1, wherein the antibody or antigen fragment thereof has a covalent bond with the surface of the exposed detection region.

7. A sensor for the detection of AMACR or an AMACR substrate thereof in a biological sample comprising:
    a substrate;
    a working electrode formed on a surface of the substrate;
    a counter electrode formed on the surface of the substrate;
    a dielectric layer covering a portion of the working electrode and counter electrode and defining an aperture exposing a detection region of the working electrode and counter electrode;
    a measuring device for applying voltage potentials to the working electrode and counter electrode and measuring the current flow between the working electrode and counter electrode; and
    an antibody or antigen binding fragment thereof directly functionalized or chemically functionalized with a surface of the exposed detection region of the working electrode so as to form a covalent bond therewith and being configured to selectively bind to AMACR or to the AMACR substrate in the biological sample, the AMACR or the AMACR substrate once bound being detectable by measuring the current flow between the working electrode and counter electrode.

* * * * *